United States Patent [19]
De Lourdes Muñoz Moreno

[11] Patent Number: 5,661,010
[45] Date of Patent: Aug. 26, 1997

[54] **PROCESS TO OBTAIN MONOCLONAL AND POLYCLONAL ANTIBODIES TO IDENTIFY PATHOGENIC AMEBIASIS AND PATHOGENIC *ENTAMOEBA HISTOLYTICA* TROPHOZOITES**

[75] Inventor: Maria De Lourdes Muñoz Moreno, Edo. De, Mexico

[73] Assignee: Centro De Investigacion Y De Estudios Avanzados Del I.P.N., Mexico

[21] Appl. No.: 567,959

[22] Filed: Aug. 15, 1990

[51] Int. Cl.$^6$ .............................. C12P 21/08; C07K 1/14; A61K 39/002
[52] U.S. Cl. ............ 435/70.2; 424/265.1; 530/412
[58] Field of Search ..................... 530/387, 387.1, 530/412; 424/88, 265.1; 435/70.21

[56] References Cited

U.S. PATENT DOCUMENTS 4,762,789  8/1988  Kune et al. ........................ 435/219

OTHER PUBLICATIONS

G. Carosi, Concepts of Structure–Function Relationships in Amoebic Organelles, pp. 288–299 (1975).

"Multilayer–Enzyme Linked Immunosorbent Assay (ML–Elisa) for Detection of *Entamoeba histolytica* Trophozoite Coproantigen", P. Anand et al., Immunological Investigations, 14(5), 443–453 (1985).

"Differentiation of Clinical Isolates of *Entamoeba histolytica* by Using Specific DNA Probes", R. Bracha et al., Jour. of Clin. Micro., Apr. 1990, pp. 680–684.

"Diagnosis of *Entamoeba histolytica* in Feces", R. Del Muro et al., Journal of Clinical Laboratory Analysis, 1:322–325 (1987).

"DNA Probes Specific for *Entamoeba histolytica* Possessing Pathogenic and Nonpathogenic Zymodemes", L. Garfinkel et al., Infection and Infection and Immunity, Mar. 1989, pp. 926–931.

"Preliminary observations using a multi–layer ELISA method for the detection of *Entamoeba histolytica* trophozoite antigens in stool samples", M.S. Grundy, Transactions of the Royal Society of Tropical Medicine and Hygiene, vol. 76, No. 3, 1982.

"Repetitive DNA Elements Characteristic of Pathogenic *Entamoeba histolytica* Strains Can Also Be Detected after Polymerase Chain Reaction in a Cloned Nonpathogenic Strain", D. Mirelman et al., Infection and Immunity, Jun. 1990, pp. 1660–1663.

"Use of the enzyme–linked immunosorbent assay (ELISA) for detection of *Entamoeba histolytica* antigen in faecal samples", G.R. Randall et al., Transactions of the Royal Society of Tropical Medicine and Hygiene (1984) 78, pp. 593–595.

"The Development and Standardization of an ELISA method for the Detection of *Entamoeba histolytica* antigens in fecal samples", D.M. Root et al., Arch. invest. Med. (Mex.) 9 (Supl. 1): 203, 1978.

"Immunological Differentiation of Pathogenic and Non-Pathogenic Isolates of *Entamoeba histolytica*", W.D. Strachan et al., The Lancet, Mar. 12, 1988, p. 562–562.

"Identification of a Pathogenic Isolate–Specific 30,000-$M_r$ Antigen of *Entamoeba histolytica* by using a Monoclonal Antibody", H. Tachibana et al., Infection and Immunity, Apr. 1990, pp. 955–960.

"The 96–Kilodalton Antigen as an Integral Membrane Protein in Pathogenic *Entamoeba histolytica*: Potential Differences in Pathogenic and Nonpathogenic Isolates", B.E. Torian et al., Infection and Immunity, Apr. 1990, pp. 753–760.

"Use of a Monoclonal Antibody in an Enzyme Immunoassay for the Detection of *Entamoeba histolytica* in Fecal Specimens", B.L. Ungar et al., Med. Hyg., 34(3), 1985, pp. 465–472.

Goding *Monoclonal Antibodies* Principles and Practice Second Edition Munoz Arch Inves. Med. 13 Supp 13 191–202 1982.

Munoz. Abstract 1919 J. Cell Biology suppl. 1988.

Calderon et al., J EAP. Med. 1980 vol. 151 p. 184.

Rojkind et al. J. Cell. Biochem 1986.

Ravdin et al Infection and immunity Jun. 1988 p. 1505 vol. 56 No. 6.

Said–Fernandez. Z. Parastenkd 1982 67(3) p. 249.

Martinez–Palomo et al. Ed. by K.P. Chang and D–Snerry. Nato ASI vol. H11 1987.

Muñoz et al. J. Exp. Med 155. 42–51 1982.

Muñoz et al. IV Journal of Protozoology, 31(3):468–470(1984) (Ref. #19).

Diamond et al. Trans. of the Royal Soc. of Inp. Medicine and Hyg.72(4):43(1978) (Ref #7).

*Molecular Biology of the Cell* 2nd Ed. 1989. p. 163. Garland Publishing Inc. (Alberts et al).

M.D.L. Munoz et al. IV Journal of Protozoology 31(3):468–470 (1984).

Diamond et al. Transactions of the Royal Society of Tropical Medicine and Hygiene 72(4):43 1978.

Molecular Biology of the Cell, Soc. Ed. Alberts et al. Garland Publishing 1989 p. 163.

*Primary Examiner*—Lila Feisee
*Attorney, Agent, or Firm*—Finnegan, Henderson, Farabow, Garrett & Dunner, L.L.P.

[57] ABSTRACT

The present invention is a process to obtain polyclonal and monoclonal antibodies useful to identify symptomatic or asymptomatic amebiasis. This invention includes the following steps: 1) Antigen preparation from electron dense granules (EDGs) secreted by *Entamoeba histolytica* trophozoites incubated in medium containing collagen type I; 2) EDG purification by differential centrifugation and 3) Production of polyclonal and monoclonal antibodies. Anti-EDG polyclonal antibodies were prepared from the serum of a goat hyperimmunized with EDGs. Monoclonal antibodies were obtained by fusion of spleen cells from Balb/c mice injected with EDG protein and SP2/O-Ag14 cells.

4 Claims, 7 Drawing Sheets

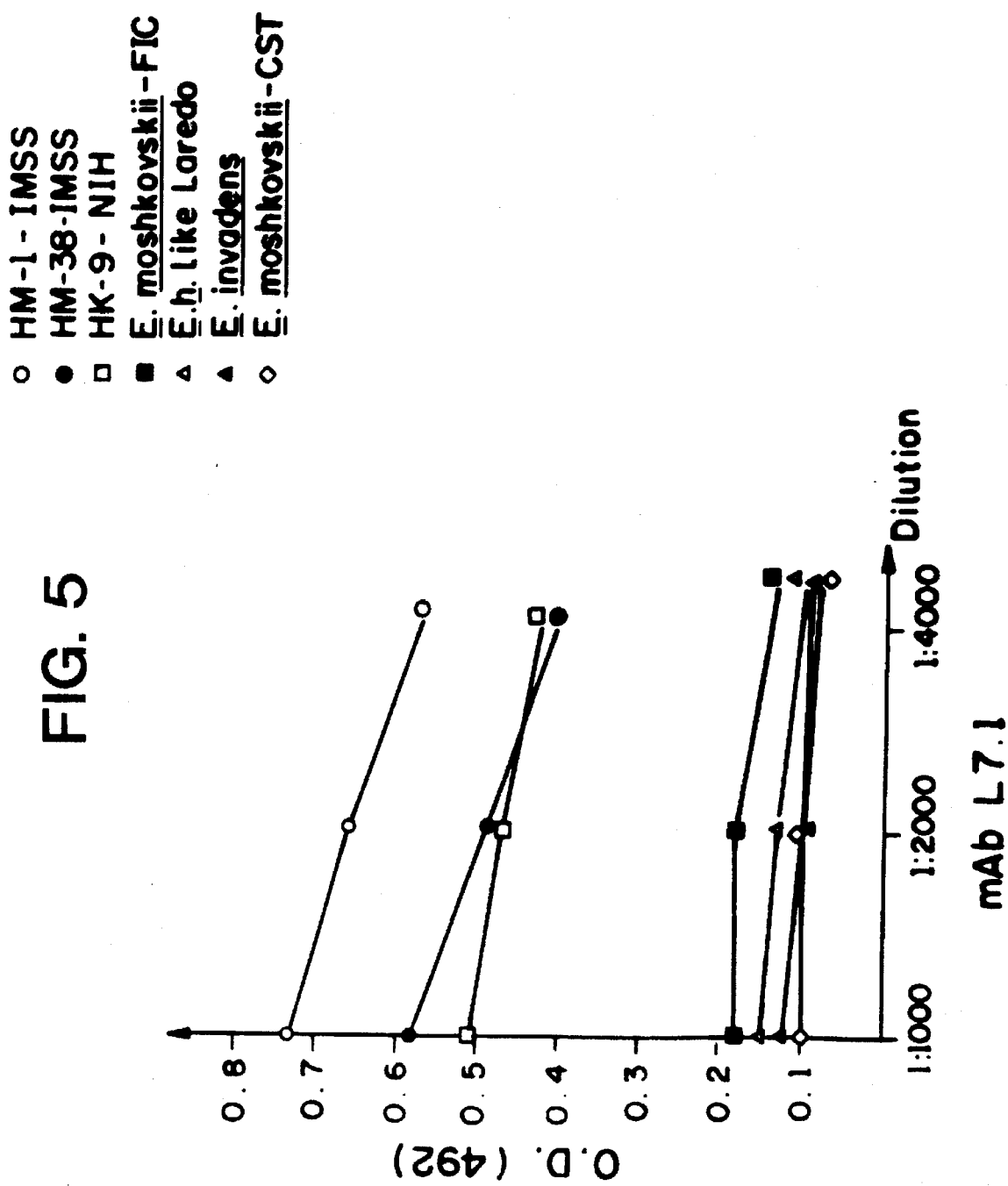

5,661,010

PROCESS TO OBTAIN MONOCLONAL AND POLYCLONAL ANTIBODIES TO IDENTIFY PATHOGENIC AMEBIASIS AND PATHOGENIC *ENTAMOEBA HISTOLYTICA* TROPHOZOITES

BACKGROUND OF THE INVENTION

Invasive amebiasis, a disease caused by the enteric protozoan *Entamoeba histolytica* is a major public health problem in developing countries (32). Recently, progress has been made in understanding the molecular bases of the pathogenesis of this disease. Thus, it has been shown that attachment of *E. histolytica* trophozoites to mammalian cells, mediated by a surface lectin, is required for direct-contact amebic cytolytic activity (20, 21, 22). An amebic protein which forms ion channels in the membranes of target cells and probably participates in cytotoxicity has also been identified (15, 33). In addition, proteolytic enzymes present on the parasite surface have been implicated in the disruption of the intestinal extracellular matrix (8, 14, 18, 19, 24).

Since collagen is a major component of the extracellular matrix, in previous works we focused our attention on the *E. histolytica* collagenase (16, 18, 19, 24). The levels of this enzyme correlate with the virulence of different *E. histolytica* strains (8, 19). The collagenase is specific for type I collagen and is localized in the plasma membrane of the trophozoite. In addition, the collagenolytic activity in trophozoites increases when they are cultured in the presence of collagen (16). In recent in vitro studies we have shown that the increase in collagenolytic activity is accompanied by the intracellular formation of electron-dense granules (EDGs). These granules accumulate in the parasite plasma membrane and are subsequently released into the extracellular milieu (16), Differences between pathogenic and non-pathogenic *E. histolytica* isolates have been observed recently using monoclonal antibodies (26) and DNA probes (3, 9, 27). However, until now there are not practical techniques to manage clinical patients.

The applicant has observed, that EDGs secreted by the parasite *E. histolytica*, contains an unknown collagenolytic activity specific for collagen type I. Consequently, this activity has been correlated with human tissue invasion.

In addition, this activity correlates with the trophozoite virulence, therefore it was considered that one or several of the EDG components may be useful in the diagnosis of pathogenic *E. histolytica* trophozoites. To test this possibility, EDGs were isolated by differential centrifugation and used as immunogen to prepare polyclonal and monoclonal antibodies specific for EDG antigens (LMT). Polyclonal antibodies were prepared from the serum of a goat hyperimmunized with EDGs. Monoclonal antibodies were prepared by fusion of Balb/c mice (immunized with EDG protein) spleen cells and the cell line SP2/O-Ag14. These antibodies were specific for EDG by ELISA, immunofluorescence and immunoelectron microscopy. These antibodies recognized *E. histolytica* from strains HM1, HM38, HK9, but did not react with the non-pathogenic trophozoites *E. moshkovskii, E. invadens,* Laredo and *E. histolytica* from asymptomatic patients in xenic culture.

INVENTION SUMMARY

The objective of this invention is to provide an assay to detect pathogenic trophozoites of *E. histolytica*. The method is a modification of the double antibody ELISA 6, 28, 29. Briefly, wells of plystyrene ELISA plates are coated with goat anti-EDG antibodies. Uncoated sites remaining are blocked with 1% BSA in PBS-T. Fecal samples in PBS-T are added and to detect EDG antigen bound to the polyclonal antibodies on the wells, these are incubated with LMT. The plates are then incubated with peroxidase-conjugated goat anti-mouse IgM and allowed to react with orthophenylene-diamine in $H_2O_2$ in the dark.

A stool sample was considered positive if the OD reading was higher than the arithmetic mean+2SD of the OD of 20 *E. histolytica*-negative control samples.

The final objective of this invention is to show that EDG antigens were detected by this assay exclusively in fecal samples of symptomatic patients but not in the asymptomatic patients. These results showed that the molecule recognized by LMT are markers of pathogenicity.

BRIEF DESCRIPTION OF DRAWINGS

FIG. 5. Binding of LMT to antigens from different strains of *E. histolytica* and other species of Entamoeba. ELISA wells coated with 10 µg of Entamoeba antigen were incubated with 1 h at 37° C. with 50 µl of the indicated dilution of LMT. Bound LMT was detected with peroxidase-conjugated goat anti-mouse IgM. In this assay, mouse polyclonal antibodies against *E. histolytica* HM1:IMSS stain cross-reacted with all Entamoeba species tested.

FIG. 7. Results of double antibody ELISA for detection of *E. histolytica* in fecal specimens. (A) Fifteen *E. histolytica*- positive samples from symptomatic individuals; (B) six *E. histolytica*-positive samples from asymptomatic individuals; (C) forty-three samples containing other parasites; and (D) twenty-five samples without parasites. This assay detects as little as 50 ng of *E. histolytica* HM1:IMSS antigen. The anti-EDG polyclonal antibodies used to coat the ELISA wells are *E. histolytica* species-specific.

DETAILED DESCRIPTION OF INVENTION

Figure 1:
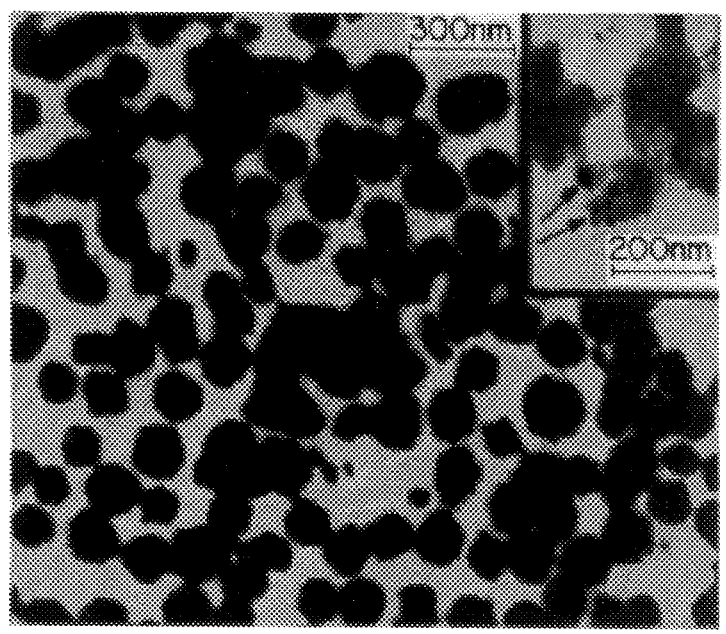
FIG. 1. Transmission electron microscope (TBM) pictograph of an EDG preparation obtained from *E. histolytica* HM1:IMSS. The inset shows and immunoelectron microscopic analysis of the same EDG preparation stained with LMT followed by rabbit anti-mouse IgM and gold-labelled protein A. The arrows point to gold particles.

This invention is related to a process to obtain monoclonal and polyclonal antibodies useful to identify pathogenic trophozoites of *E. histolytica*. TYI-S-33 medium can be modified by the elimination of L-cystein, serum and vitamins and the addition of 1 mM calcium. It includes:

a) Preparation of antigen from *E. histolytica* trophozoites incubated in TYI-S-33M (18) containing collagen type I.

Induction of EDG release by collagen. Trophozoites of *E. histolytica* HM1:IMSS ($10^6$/ml) were resuspended in medium TYI-S-33M (18) containing collagen type I (0.3 mg/ml) and Carbecin (5.5 µg/ml) are incubated for 16 h at 37° C.

The incubation medium TYI-S-33 (7) also can be modified by the elimination of L-Cysteine, serum and vitamins, and the addition of 1 mM $Ca^{2+}$. *E. histolytica* trophozoites incubated in a medium containing collagen induce a significant increase in the formation and liberation of EDGs.

b) EDG secreted in (a) are isolated from the culture medium by differential centrifugation where the trophozoite can be sedimented by centrifugation intervals of 500 to 1,200 rpm. Cellular fragments can be sedimented by centrifugation intervals of 2,000 to 2,500 rpm and EDG can be sedimented by centrifugation intervals of 9,000 to 11,000 rpm at temperatures lower than room temperature.

Isolation of EDG. After trophozoite incubation for 16 h at 37° C. as described in "(a)", the cells were chilled (4° C.) and collected by centrifugation (230 g for 5 min). The supernatant containing released EDGs was centrifuged for 10 min at 650 g to remove debris and then EDGs were pelleted at 13,000 g for 15 min and resuspended in Ringer solution. Protein was determined by the Lowry assay (13) using bovine serum albumin as a standard.

c) EDG collagenase activity is detected by a colorimetric method described by the applicant.

Collagenase assay. Human collagen type I was extracted from placentas as described previously (18). For the collagenase assay, aliquots of type I collagen (20 µl; 3 mg/ml) in 0.05M Tris-HCl buffer pH 7.2 were added to each well of tissue culture multiwell plates (model 76-003-05, Linbro, Chemical Co., Hamden, Conn.). The plates were incubated at 37° C. for 1 h and then, after sterilization with U.V. light, the collagen films were incubated for 3 h at 37° C. with EDG (10, 100, 200 and 400 µg/ml) resuspended in Ringer solution containing 5. 5 µg/ml Carbecin (a gift of Laboratorios Sanfer, Mexico, D.F.). After incubation the films were fixed in 2.5% (wt/vol) glutaraldehyde, washed and stained with picrosirius solution (0.1% sirius red in saturated aqueous picric acid) for 1 h (10). Excess dye was washed out three times with 0.1N HCl and the dye bound collagen was eluted with 200 µl of 0.1N NaOH in absolute methanol (1:1). Then, samples diluted 1:10 were read in a spectrophotometer at 540 nm. A unit of collagenase was defined as the enzymatic activity able to digest 1 µg of collagen/min at 37° C. (18).

d) Monoclonal and polyclonal antibodies preparation.

The immunogen may be prepared with an inflammatory agent in order to allow for a better immune response.

The EDG rich pellet was used as the antigen to produce monoclonal antibodies in mice. Balb/c mice were subcutaneously injected with 150 µg of EDG protein in 300 µl PBS emulsified with 300 µl complete Freund's adjuvant. Eighteen days later the mice were inoculated intraperitoneally with 150 µg of antigen in PBS and three days later their spleens were removed for fusion. Cell fusion was carried out with polyethylene glycol according to standard procedures (11) using the cell line SP2/O-Ag14 (25). Initial screening of culture supernatants was performed by ELISA (31) using *E. histolytica* HM1:IMSS total antigen. Purified EDGs were used as the antigen for the secondary screening of supernatants. Cells were subcloned by limiting dilution and three hybridoma lines (LMI, LMT and LMB) were obtained. All Mab's were of the IgM class. They were either used as culture supernatants or in ascites form with identical results. For most experiments hybridoma LMT was chosen because it is a better antibody secretor.

Anti-EDG polyclonal antibodies were prepared from the serum of a goat hypermimmunized with EDGs. Balb/c mouse antiserum to strain HM1:IMSS was produced by two i.p. immunization with $2 \times 10^6$ live trophozoites each time.

The next examples show the utility of the polyclonal and monoclonal antibodies anti-EDG.

EXAMPLE 1

ELISA for fecal samples. The method used was a modification of the double antibody ELISA'S described by Ungar et al (28, 29) and Del Muro et al (6). All washing procedures were performed three times with PBS containing 0.05% Tween-20 (PBS-T). Wells of polystyrene ELISA plates (Immulon I, Dynatech Laboratories, Alexandria, Va.) were coated with goat anti-EDG antibodies (100 µg/0.1 ml) in 0.1M carbonate buffer pH 9.6 and incubated overnight at 4° C. Uncoated sites remaining were blocked with 1$ BSA in PBS-T and the wells were washed as described before. Fecal samples in PBS-T (50 µl) were added and incubated for 2 h at 37° C. and washed as above. To detect EDG antigen bound to the polyclonal antibodies on the wells, these were incubated for 1 h at 37° C. with LMT diluted 1:1,000 in 1% BSA-PBS-T. The plates were washed and 50 µl of a 1:1,000 dilution of peroxidase-conjugated goat anti-mouse IgM (Zymed Laboratory, South San Francisco, Calif.) was added. After incubation for 1 h at 37° C. the plates were washed again and 100 µl of orthophenylenediamine in $H_2O_2$ was added and allowed to react in the dark for 30 min at room temperature.

A stool sample was considered positive if the OD reading was higher than the arithmetic mean+2 SD of 25 *E. histolytica*-negative control samples.

EXAMPLE 2

Immunoprecipitation. Five million *E. histolytica* trophozoites from logarithmic-phase cultures were incubated for 6 h in 3 ml of serum-free TYI-S-33 medium containing 600 µCi of [$^{35}$S]methionine (1209 Ci/mmol, New England Nuclear, Boston, Mass.). Trophozoites were harvested, washed twice with cold PBS containing 0.27M NaCl and solubilized by vortexing in 40 mM Tris buffer pH 7.5 containing 150 mM NaCl, 1% Triton X-100, 2 mM EDTA, 2 mM phenylmethyl sulfonyl fluoride (PMSF), and 1 mM p-hydroximercuribenzoate (PHMB). The samples were stored at −70° C. until used. Before immunoprecipitation, insoluble material was removed from the lysate by centrifugation at 16,000 g for 10 min at 4° C. For immunoprecipitation the LMT was bound to affinity-purified rabbit anti-mouse IgM which was previously linked to protein A-Sepharose beads (Pharmacia Fine Chemicals, Piscataway, N.J.) as described by Yuan et al (34). Fifty μl of rabbit anti-mouse IgM-protein A-Sepharose was incubated for 4 h at 4° C. with continuous rotation, with 100 μl of a 1 mg/ml solution of LMT. Thereafter, the Sepharose beads were washed twice with PBS and incubated for 3 h at 4° C. with 100 μl of lysate containing $5 \times 10^5$ labeled amebas. After incubation, the beads were washed twice with PBS containing 0.5% Triton X-100 and after an additional wash with PBS the beads were boiled in 100 μl of 4 X SDS-PAGE sample buffer, centrifuged and the supernatant loaded on 10% SDS-PAGE Laemmli gels (12). After electrophoresis, the gels were fixed and processed for fluorography (2).

EXAMPLE 3

Immunofluoroscence. Trophozoites were fixed for 15 min with 1.85% formaldehyde and 0.125 glutaraldehyde at 37° C., washed with PBS and incubated with 1M glycine for 15 min at 37° C. Afterwards, the cells were permeabilized with 0.3% (w/v) Triton X-100 in 15 mM phosphate buffer pH 7.2, containing 180 mM NaCl, and washed three times with the same solution. They were then incubated with 0.0025% Evans blue for 20 min at 37° C. and finally treated with MAb LMT (ascites fluid diluted 1:50) overnight at 4° C. After washing with PBS, the cells were incubated with fluorescein-conjugated goat anti-mouse IgM (Hyclone laboratories, Inc. Utah). Excess antibody was removed by washing three times with PBS. The trophozoites were mounted in 50% glycerol and then observed by fluorescence microscopy.

EXAMPLE 4

Immunoelectron Microscopy. Trophozoites, incubated for 6 h with collagen (0.3 mg/ml), were fixed in a mixture of 0.125% glutaraldehyde and 1.85% formaldehyde in PBS for 15 min at 37° C. After permeabilization with 0.3% Triton X-100 the cells were washed 3 times in PBS and incubated for 30 min at room temperature with 50 μl of rabbit anti-mouse IgM diluted 1:200. After three PBS washes, the cells were incubated with 10 μl of protein A/colloidal gold diluted 1:2. Finally, the cells were fixed with 2.5% glutaraldehyde and processed for electron microscopy (30). Negative controls included normal ascites fluid or omission of monoclonal antibody.

EXAMPLE 5

Parasites. E. histolytica strains HM1:IMSS, HM38:IMSS and HK9 were cultured axenically in TYI-S-33 medium (7) at 37° C. E. moshkovskii-FITC, E. moshkovskii-CST, E. invadens and E. histolytica-like Laredo were cultivated in the same medium at 25° C. Strains HK9, E. moshkovskii-CST and Laredo isolates were kindly provided by Dr. L. S. Diamond (National Institutes of Health, Bethesda, Md.). Axenic E. histolytica strains HM1:IMSS, HM38:IMSS and HK9 were all originally isolated from patients with active amebic disease and have pathogenic type zymodeme. E. invadens is a specie which infects reptiles whereas E. moshkovskii strains CST and FIC, originally isolated from sewage water, have no known host. E. histolytica-like Laredo is generally considered as a species different from E. histolytica and taxonomically closer to E. moshkovskii (1).

Five E. histolytica isolates (HM42:IMSS, HM43:IMSS, HM44:IMSS, HM46:IMSS and HM47:IMSS) from stools of asymptomatic carriers (17) and one isolate (HM48:IMSS) from a patient with amebic dysentery were all grown in xenic cultures in modified (5) Boch and Drbohlav's medium. Isolates HM42:IMSS to HM47:IMSS have non-pathogenic zymodeme (17) and were obtained from donors without symptom and showing no clinical, serological or endoscopic signs of amebic intestinal invasion (17).

According with the above examples the next results were determined:

EDG are enriched in collagenase. We have previously shown that incubation of trophozoites with collagen induces the formation of EDGs which accumulate in the parasite plasma membrane and are subsequently released into the extracellular medium (16). Concomitantly, there was a large increase in plasma membrane-bound collagenolytic activity, associated with degradation of collagen. Therefore, we hypothesized that EDGs are related to the lytic properties of the trophozoites and that they might contain collagenase (16,24). To test this possibility, a preparation highly enriched in EDGs was obtained from supernatants of trophozoites cultured in the presence of collagen. By TEM, no structures other than EDGs were observed in such preparation (FIG. 1). When the collagenolytic activity of the purified EDGs was measured using collagen type I as a substrate, 1.66 units of collagenase were detected per mg of EDGs protein. This specific activity is approximately ten- and twenty-four-fold higher than that found in whole trophozoites incubated with and without collagen, respectively. These results suggest that EDGs participate in the packing and secretion of collagenase, and therefore, may plate a role in tissue destruction during invasive amebiasis.

Figure 2:
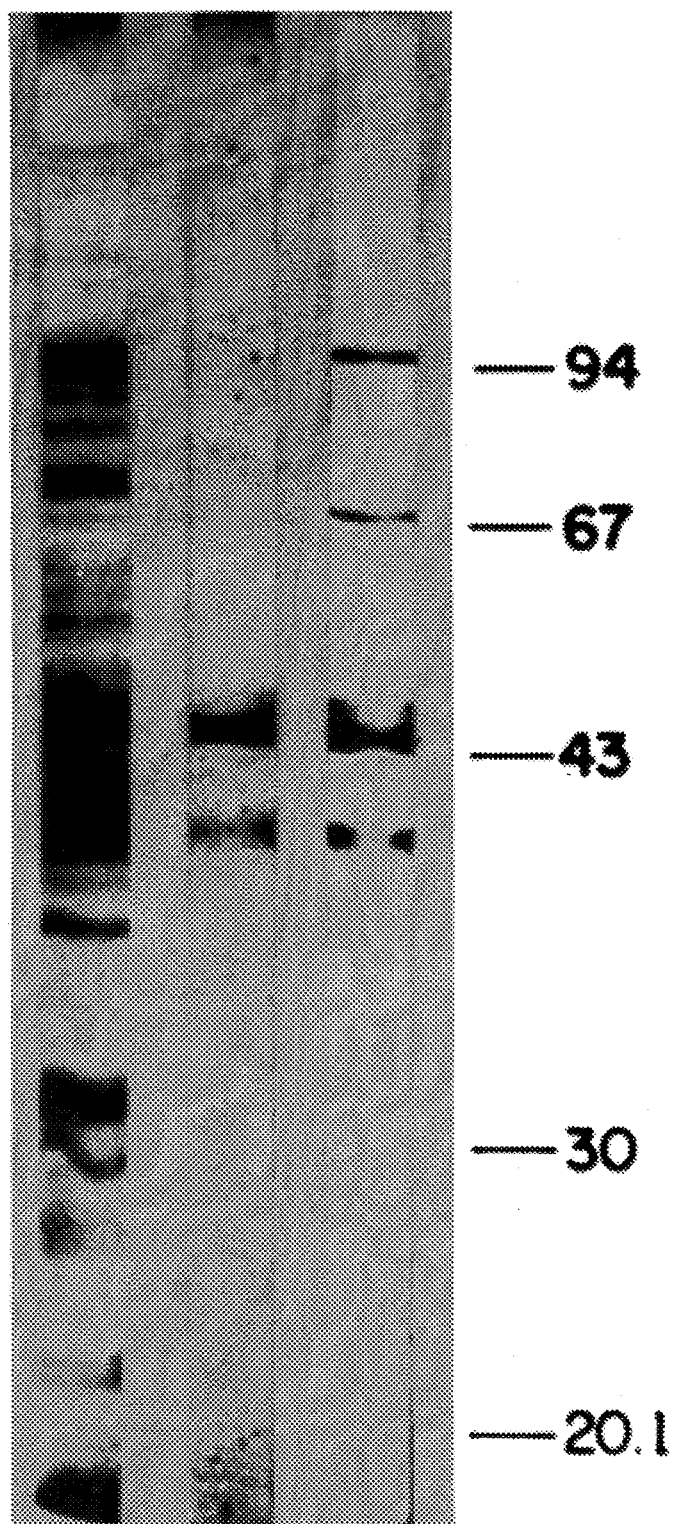
FIG. 2. Immunoprecipitation of [$^{35}$S]methionine-biosynthetically-labelled *E. histolytica* HM1:IMSS antigens. Lane A, SDS-PAGE profile of whole [$^{35}$S]methionine-labelled trophozoites; lane B, polypeptides precipitated with rabbit anti-mouse IgM bound to protein A-Sepharose; lane C, polypeptides precipitated with LMT attached to rabbit anti-mouse IgM-protein A-Sepharose.

Monoclonal antibodies against EDG. To characterize EDGs further, we prepared monoclonal antibodies against them. Of the 20 clones that secreted antibodies reacting with total E. histolytica antigen, three IgM (LMI, LMT and LMB) that also bound to EDG coated ELISA plates were selected. Their reaction with purified EDGs was also demonstrated by immunoelectron microscopy (FIG. 1, inset). LMT was used for most experiments because it could be obtained in larger quantities than LMI or LMB. By immunoprecipitating [$^{35}$S] methionine-metabolically labeled E. histolytica HM1:IMSS antigens with LMT we could detect the specific precipitation of two polypeptides having mol wt of 95,000 and 68,000 (FIG. 2). Two additional polypeptides of 45,000 and 40,000 Da were nonspecifically precipitated and are also seen in control immunoprecipitates without LMT. Presumably, this LMT is not directed to collagenase because the molecular weight of the immunoprecipitated polypeptides do not agree with that which we have recently found for collagenase (unpublished observations). In addition, LMT failed to inhibit the collagenolytic activity of trophozoites (data not shown).

Figure 3A:
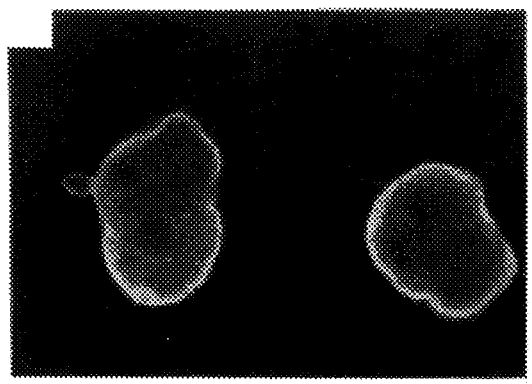
FIG. 3. Immunofluorescence microscopy of *E. histolytica* HM1:IMSS trophozoites stained with anti-EDG monoclonal antibody LMT. (A) Trophozoites cultured without collagen and stained with LMT, (B–D) trophozoites incubated with collagen for: (B) 3 h, (C) 6 h, or (D) 16 h; (E) trophozoites incubated with collagen (16 h) and stained with non-specific mouse immunoglobulin.
Figure 3B:
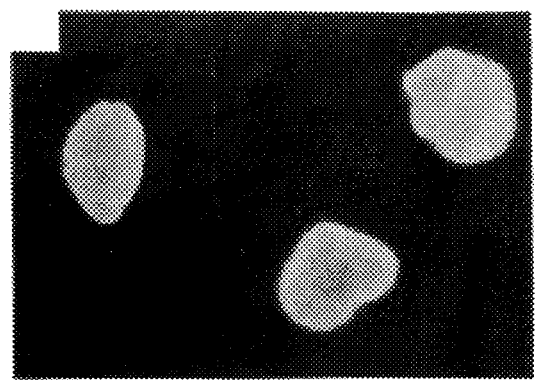
Figure 3C:
Figure 3D:
Figure 3E:
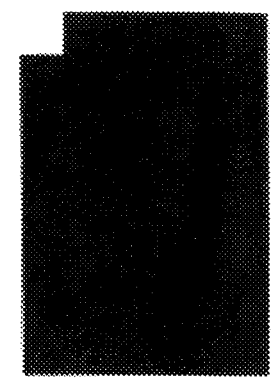
Figure 4A:
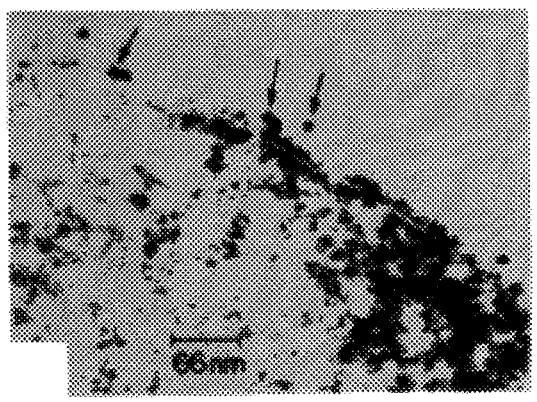
FIG. 4. Colloidal gold immunoelectron microscopy of *E. histolytica* HM1:IMSS trophozoites. (A) Trophozoites cultured without collagen; (B–D) trophozoites incubated with collagen for 6 h. The cells were fixed and treated with LMT followed by rabbit anti-mouse IgM and gold-labelled protein A. Note the gold particles (arrows) in electron-dense areas close to microtubule like structures (B) and in electron-dense granules (C–D).
Figure 4B:
Figure 4C:
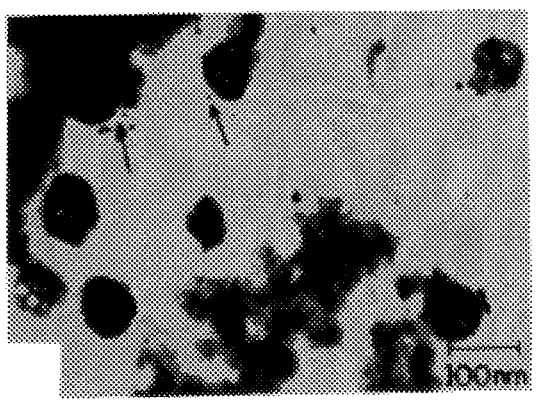
Figure 4D:
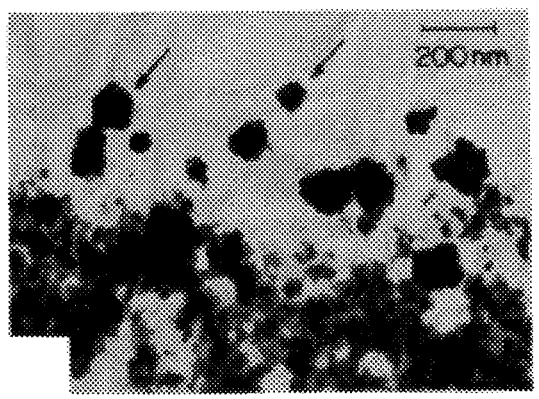

In order to further understand the events leading to the assembly of EDG antigens, trophozoites were incubated with and without collagen. Both Mab's (LMI and LMT) yielded identical staining patterns by indirect immunofluorescence. In trophozoites incubated without collagen fluorescence was localized mostly in the membrane and more than 90% of the trophozoites were labeled (FIG. 3A). After 3 of incubation in liquid medium containing collagen a similar staining pattern was observed and fluorescence was increased (FIG. 3B). After 6 h of incubation, the number of labeled trophozoites decreased to approximately 70% and the fluorescence was localized in the peripheral cytoplasm and the plasma membrane (FIG. 3C). After 16 h of incubation with collagen, trophozoites showed significantly diminished membranal and cytoplasmic fluorescence and only an estimated 10% of the cells were labeled (FIG. 3D). Trophozoites treated with non-specific mouse Ig or with fluoresceinated second antibody along showed no fluorescence (FIG. 3E). Colloidal gold innmunoelectron microscopy studies with LMT confirmed and extended the immunofluorescence findings. Gold particles were only found in the plasma membrane of trophozoites not incubated with collagen (FIG. 4A). EDGs were not observed. In trophozoites incubated for 6 h with collagen, labeled EDGs were found in the cytoplasm, beneath the plasma membrane and extracellularly (FIGS. 4C–D). Dispersed labeling of plasma membrane was also observed. In these trophozoites, the gold particles were also found in electron-dense zones close to microtubule-like structures (FIG. 4B). In summary, these studies revealed that the EDG antigen detected by LMT is redistributed in the trophozoites after their interaction with collagen. Furthermore, after prolonged incubation the antigen was lost from trophozoites as evidenced by lack of staining in immunofluorescence. This antigen loss is due presumably to the release of EDGs into the extracellular medium. The findings indicate that molecules initially present in the plasma membrane are incorporated into EDGs. However, the data does not allow the site of EDGs assembly to be located precisely.

Figure 6:
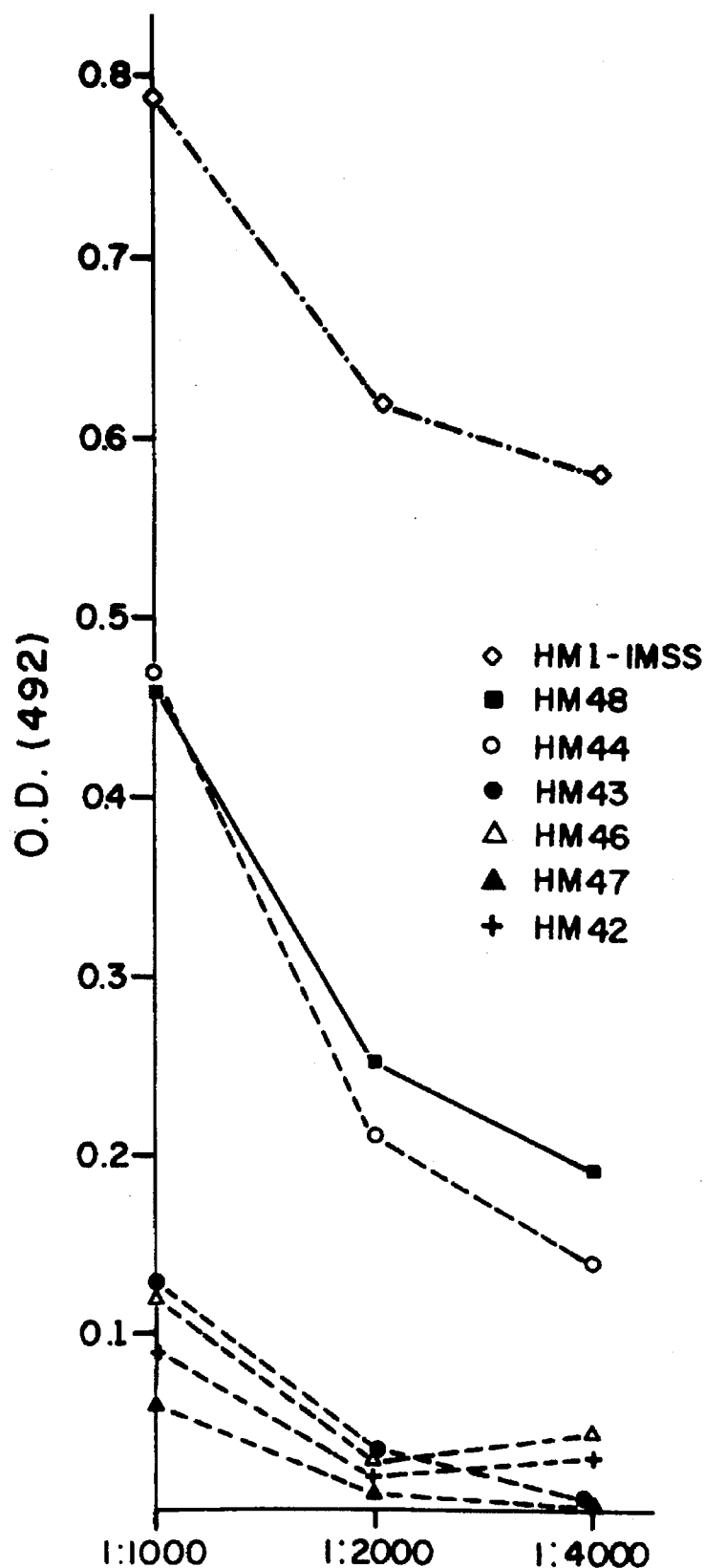
FIG. 6. Binding of LMT to *E. histolytica* clinical isolates. -.-.-.-, axenic strain HM1:IMSS:____, isolate HM48:IMSS, from a patient with symptoms of amebiasis; -----, isolates with non-pathogenic zymodeme from asymptomatic individuals (HM42:IMSS, HM43:IMSS, HM44:IMSS, HM46:IMSS, HM47:IMSS). For the assay, ELISA wells coated with 10 µg of antigen from the different isolates were incubated for 1 h at 37° C. with 50 µl of the indicated dilution of LMT. Bound LMT was detected with peroxidase-conjugated goat anti-mouse IgM.

Strain specificity of monoclonal antibodies. Reactivity of LMT and LMI were tested against antigens from trophozoites of three axenic strains of *E. histolytica* (HM1:IMSS, HM38:IMSS and HK9-NIH) which posses pathogenic zymodeme, and from other species of Entamoeba such as *E. moshkovskii*-FITC, *E. moshkovskii*-CST, *E. invadens* and *E. histolytica*-like Laredo. Results of the ELISA assays for LMT are shown in FIG. 5. LMI showed identical specificity. The Mab's recognized only the three *E. histolytica* strains. In contrast, mouse polyclonal antibodies to *E. histolytica* HM1:IMSS cross-reacted with all Entamoeba species (data not shown). LMT was also tested against *E. histolytica* clinical isolates maintained in xenic culture (FIG. 6). One isolate (HM48:IMSS) from a patient with clinical symptoms of amebiasis gave a strong positive reaction in the ELISA. In contrast, of five additional isolates obtained from asymptomatic carriers only one (HM44:IMSS) was positive. These five cultures have non-pathogenic zymodeme and were isolated from individuals free of gastrointestinal symptoms, and negative in serological assay and rectosigmoidoscopy (17). In summary, all *E. histolytica* axenic strains and clinical isolates obtained from invasive cases of amebiasis gave a positive reaction with LMT whereas most of the isolates from asymptomatic patients were negative. These results suggest that expression of the epitope recognized by LMT correlate with pathogenic potential of the *E. histolytica* strains. The reaction of LMT with isolate HM44:IMSS possessing nonpathogenic zymodeme may possibly reflect the variability in virulence levels of isolates with nonpathogenic zymodemes (4). Exceptions in correlations between zymodeme pattern and expression of putative virulence factors have been noted by others (23).

Figure 7:
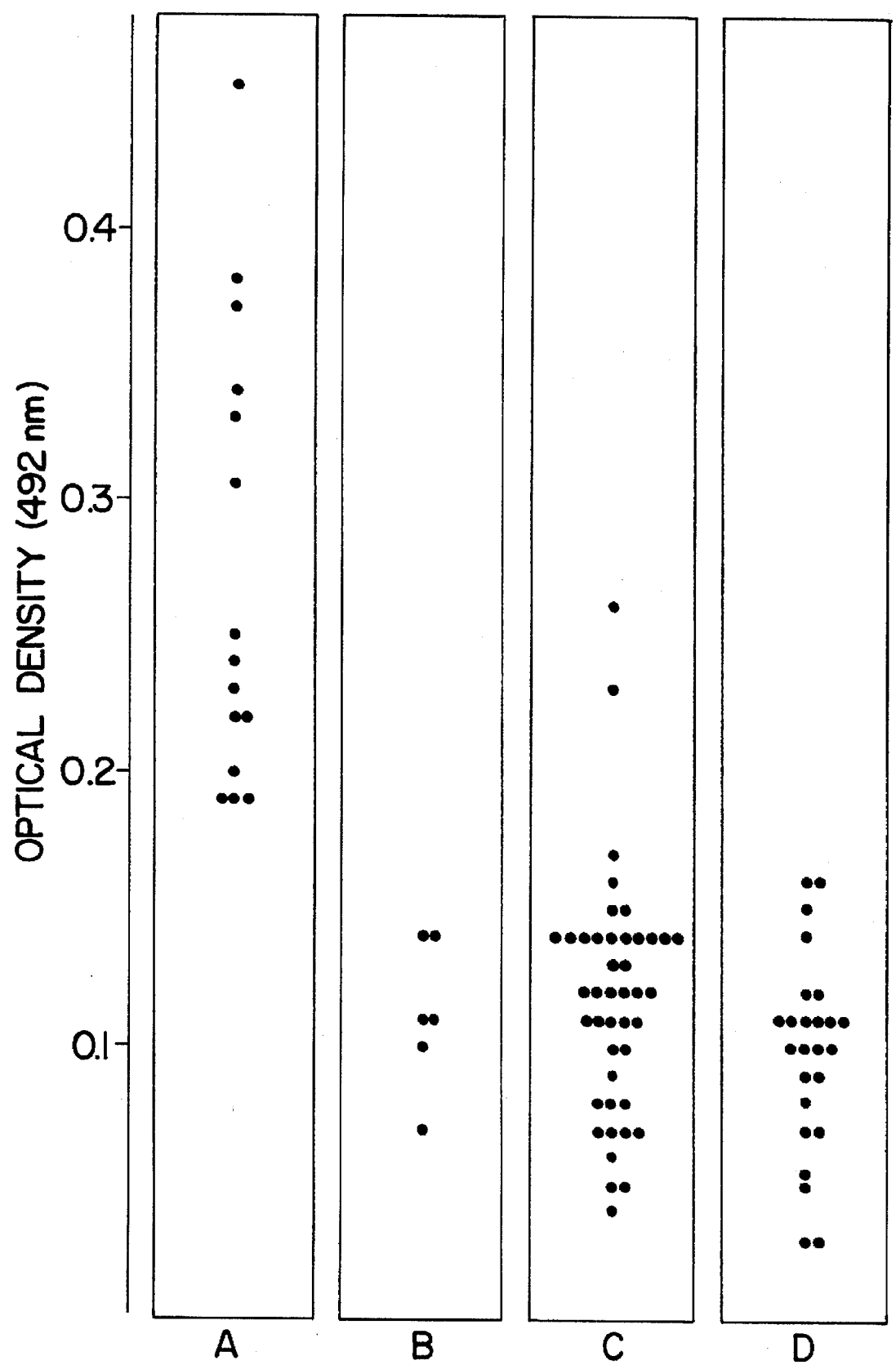

Detection of EDG components in stool samples. The above finding prompted us to explore the feasibility of using the anti-EDG LMT to detect *E. histolytica* in stool samples. LMT was used in combination with goat polyclonal anti-EDG (antibodies specific for the species *E. histolytica*) to develop a double antibody ELISA (FIG. 7). Fifteen of the 21 specimens were positive. These 15 positive samples were obtained from patients with classical symptoms of amebic dysentery. In contrast, the 6 ELISA-negative stool samples came from asymptomatic individuals in which cysts were incidentally found during routine microscopic stool examination. As specificity controls for the ELISA, 68 fecal samples without *E. histolytica* were examined. Forty-three of these samples contained other parasites such as *Entamoeba coli, Endolimax nana, Ascaris lumbricodoies, Trichuris trichiura,* Hymenolepis and *Giardia lamblia*. All 25 samples without parasites, as determined by microscopy, yielded negative results in the ELISA identifies pathogenic symptomatic or asymptomatic amebiasis ELISA (FIG. 7). Forty-one of the 43 samples containing parasites other then *E. histolytica* were also negative. The finding of positive ELISA as compares with microscopy for the detection of intestinal amebiasis (6,29,30).

These results further suggest that LMT may identify invasive strains of *E. histolytica*. Differences between pathogenic and nonpathogenic *E. histolytica* isolates have been observed recently using monoclonal antibodies (26) and DNA probes (3,9,27). Our monoclonal antibodies against EDGs may be an additional tool to investigate the bases for *E. histolytica* pathogenicity.

LITERATURE CITED

1. Bhattacharya, S., A. Bhattacharya, and L. S Diamond. 1988. Comparison of repeated DNA from stains of *Entamoeba histolytica* and other Entamoeba. Mol. Biochem. Parasitol. 27:257–262.
2. Bonner, W. M. 1984, Fluorography for the detection of radioactivity in gels. Methods Enzymol. 104:460–465.
3. Bracha, R., L. S. Diamond, J. P. Ackers, G. D. Burchard, and D. Mirelman. 1990. Differentiation of clinical isolates of *Entamoeba histolytica* by using specific DNA probes. J. Clin. Microbiol. 28:680–684.
4. Burchard, G. D., and D. Mirelman. 1988. *Entamoeba histolytica*: virulence potential and sensitivity to metronidazole and emetine of four isolates possessing nonpathogenic zymodemes. Exp. Parasitol. 66:231–242.
5. De la Torre, M., L. Landa, and B. Sepúlveda. 1970. Avances en los métodos para el cultivo de *Entamoeba histolytica*.
6. Del Muro, R., A. Oliva, P. Herion, R. Capín, and L. Ortiz-Ortiz. 1987. Diagnosis of *Entamoeba histolytica* in feces by ELISA. J. Clin. Lab. Anal. 1:322–325.
7. Diamond, L. S. , D. R. Harlow, and C. C. Cunnick. 1978. A new medium for the axenic cultivation of *Entamoeba histolytica* and other Entamoeba. Trans. R. Soc. Trop. Med. Hyg. 72:431 432.
8. Gadasi, H., and E. Kessler. 1983. Correlation of virulence and collagenolytic activity in *Entamoeba histolytica*. Infect Immun. 39:528–531.
9. Garfinkel, L. I., M. Giladi, M. Huber, C. Gitler, D. Mirelman, M. Revel, and S. Rozenblatt. 1989. DNA probes specific for *Entamoeba histolytica* possessing pathogenic and nonpathogenic zymodemes. Infect. Immun. 57:926–931.
10. Junqueira, L. C. U., G. Bignolas, and R. R. Brentani. 1979. A simple and sensitive method for the quantitative estimation of collagen. Anal. Biochem. 94:96–99.
11. Kennet, R.-H. 1979. Cell fusion. Methods Enzymol. 58:345–359.
12. Laemmli, U. K. 1979. Cleavage of structural proteins during the assembly of the head of bacteriophage T4. Nature (London) 227:680–685.
13. Lowry, O. H., N. J. Rosebrough, A. L. Far, and R. J. Randall. 1951. Protein measurements with the Folin phenol reagent. J. Biol. Chem. 193:265–275.
14. Lushbaugh, W. B. 1988. Proteinases of *Entamoeba histolytica* p. 219–231. In J. I. Ravdin (ed.), Amebiasis: human infection by *Entamoeba histolytica*. John Wiley & Sons, Inc., New York.
15. Lynch, E. C., I. M. Rosenberg, and C. Gitler. 1982. An ion-channel forming protein produced by *Entamoeba histolytica*. EMBO J. I:801–804.

16. Martínez-Palomo, A., I. Meza, B. Chávez, J. L. Rosales-Encina, M. L. Muñoz, A. González-Robles, and M. Rojkind. 1987. *Entamoeba histolytica*: activation and release of membrane dense bodies, p. 371–376. In K.-P. Chang and D. Snary (ed.), Host-parasite cellular and molecular interactions in protozoal infections. NATO ASI Series, vol. H. 11. Springer-Verlag KG. Berlín.

17. Meza, L., M. De la Garza, M. A. Meraz, B. Gallegos, M. De la Torre, M. Tanimoto, and A. Martínez-Palomo. 1986. Isoenzyme patterns of *Entamoeba histolytica* isolates from asymptomatic carriers: use of gradient acrylamide gels. Am. J. Trop. Med. Hyg. 35:1134–1139.

18. Muñoz, M. L., J. Calderón, and M. Rojkind. 1982. The collagenase of *Entamoeba histolytica*. J. Exp. Med. 155-42–51.

19. Muñoz, M. L., M. Rojkind, J. Calderón, M. Tanimoto, S. Arias-Negrete and A. Martínez-Palomo. 1984. *Entamoeba histolytica*: collagenolytic activity and virulence. J. protocol. 31:468–470.

20. Petri, W. A., Jr., R. D. Smith, P. H. Schlesinger, and J. I. Ravdin. 1987. Isolation of the galactose-binding lectin which mediates the invitro adherence of *Entamoeba histolytica*. J. Clin. Invest. 80:1238–1244.

21. Ravdin, J. I., B. Y. Croft, and R. L. Guerrant. 1980. Cytopathogenic mechanisms of *Entamoeba histolytica*. J. Exp. Med. 152:377–390.

22. Ravdin, J. I., and R. L. Guerrant. 1981. Role of adherence in cytopathogenic mechanisms of *Entamoeba histolytica*: study with mammalian tissue culture cells and human erythrocytes. J. Clin. Invest. 68:1305–1313.

23. Reed, S. L., W. E. Keene, and J. H. McKerrow. 1989. Thiol proteinase expression and pathogenicity of *Entamoeba histolytica*. J. Clin. Microbiol. 27:2772–2777.

24. Rojkind, M., J. L. Rosales-Encina, and M. L. Muñoz. 1988. The collagenase of *Entamoeba histolytica*, p. 263–272. In J. I. Ravdin (ed.). Amebiasis: human infection by *Entamoeba histolytica*. John Wiley & Sons, Inc., New York.

25. Shulman, M., C. D. Wilde, and G. Köhler. 1978. A better cell line for making hybridomas secreting specific antibodies. Nature (London) 276:269–270.

26. Strachan, W. D., P. L. Chiodini, W. M. Spice, A. H. Moody, and J. P. Ackers. 1988. Immunological differentiation of pathogenic and non-pathogenic isolates of *Entamoeba histolytica*. Lancet i:561–563.

27. Tannich, E., R. D. Horstmann, J. Knobloch, and H. H. Arnold. 1989. Genomic DNA differences between pathogenic and non-pathogenic *Entamoeba histolytica*. Proc. Natl. Acad. Sci. USA 86:5118–5122.

28. Ungar, B. L. P., R. H. Yolken, T. E. Nash, and T. C. Quinn. 1984. Enzyme-linked immunosorbent assay for the detection of *Giardia lamblia* in fecal specimens. J. Infect. Dis. 149:90–97.

29. Ungar, B. L. P., R. H. Yolken, and T. C. Quinn. 1985. Use of a monoclonal antibody in an enzyme immunoassay for the detection of *Entamoeba histolytica* in fecal specimens. Am. J. Trop. Med. Hyg. 34:465–472.

30. van Deurs, B., T. I. Tonnessen, O. W. Petersen, K. Sandvig, and S. Olsnes. 1986. Routing of internalized ricin and ricin conjugates to the golgi complex. J. Cell. Biol. 102-37–47.

31. Voller, A., and D. Bidwell. 1986. Enzyme-linked immunosorbent assay, p. 99–109. In N. R. Rose, H. Friedman, and J. L. Fahey (ed.). Manual of clinic laboratory immunology, 3rd ed. American Society for Microbiology, Washington, D.C.

32. Walsh, J. A. 1986. Problems in recognition and diagnosis of amebiasis: estimation of the global magnitude of morbidity and mortality. Rev. Infect. Dis. 8:228–238.

33. Young, J. D., T. M. Young, L. P. Lu, J. C. Unkeless, and Z. A. Cohn, 1982. Characterization of a membrane pore-forming protein from *Entamoeba histolytica*. J. Exp. Med. 156:1677–1690.

34. Yuan, L., J. C. Barriocanal, J. S. Bonifacino, and I. V. Sandoval. 1987. Two integral membrane proteins located in the cis-middle and trans-part of the Golgi system acquire sialylated N-linked carbohydrates and display different turnovers and sensitivity to cAMP dependent phosphorylation. J. Cell. Biol. 105-215–227.

I claim:

1. A process to obtain an antibody specific to electron dense granules (EDGs) of pathogenic *Entamoeba histolytica* trophozoites, wherein said antibody is capable of distinguishing pathogenic trophozoites from nonpathogenic trophozoites, comprising the steps of:

a) incubation *Entamoeba histolytica* trophozoites in TY1-S-33 medium modified by the elimination of L-cystein, serum and vitamins and the addition of type I collagen and calcium, b) isolating EDGs from the medium, and c) immunizing a non-human mammal with the isolated EDGs.

2. A process, as claimed in claim 1, wherein the EDGs are isolated from the medium by differential centrifugation at a temperature below room temperature and wherein trophozoites are sedimented at 500 to 1200 rpm, cellular fragments are sedimented at 2000 to 2500 rpm, and EDGs are sedimented at 9000 to 11000 rpm.

3. A process, as claimed in claim 1, wherein the antibody is a polyclonal antibody obtained from the serum of the immunized non-human mammal.

4. A process, as claimed in claim 1, wherein the antibody specific to EDGs is a monoclonal antibody obtained by the further steps of:

a) isolating a spleen cell from the non-human mammal, b) fusing the spleen cell with a suitable fusion partner to form a hybridoma, and c) obtaining the monoclonal antibody from the hybridoma.

* * * * *